United States Patent
Dees et al.

(10) Patent No.: US 7,036,516 B1
(45) Date of Patent: May 2, 2006

(54) TREATMENT OF PIGMENTED TISSUES USING OPTICAL ENERGY

(75) Inventors: H. Craig Dees, Knoxville, TN (US); Eric A. Wachter, Oak Ridge, TN (US)

(73) Assignee: Xantech Pharmaceuticals, Inc., Knoxville, TN (US)

( * ) Notice: Subject to any disclaimer, the term of this patent is extended or adjusted under 35 U.S.C. 154(b) by 540 days.

(21) Appl. No.: 09/130,213

(22) Filed: Aug. 6, 1998

Related U.S. Application Data

(63) Continuation-in-part of application No. 08/739,801, filed on Oct. 30, 1996, now Pat. No. 5,829,448.

(51) Int. Cl.
*A61B 19/00* (2006.01)

(52) U.S. Cl. .............. 128/898; 604/20

(58) Field of Classification Search ............. 607/88, 607/89, 92; 606/9, 13, 14; 604/20; 128/898
See application file for complete search history.

(56) References Cited

U.S. PATENT DOCUMENTS

| | | | |
|---|---|---|---|
| 4,378,806 A | 4/1983 | Henley-Cohn | 128/504 |
| 4,490,543 A | 12/1984 | Bergquist et al. | |
| 4,601,037 A | 7/1986 | McDonald | 372/25 |
| 4,647,578 A | 3/1987 | Crounse et al. | |
| 4,822,335 A * | 4/1989 | Kawai et al. | 604/20 |
| 4,846,789 A | 7/1989 | Heitz et al. | |
| 4,891,043 A | 1/1990 | Zeimer et al. | 604/20 |
| 4,973,848 A * | 11/1990 | Kolobanov et al. | 250/458.1 |
| 5,034,613 A | 7/1991 | Denk et al. | 250/458 |
| 5,050,597 A * | 9/1991 | Daikuzono | 128/395 |
| 5,066,291 A | 11/1991 | Stewart | 606/3 |
| 5,089,384 A | 2/1992 | Hale | 435/2 |
| 5,099,756 A | 3/1992 | Franconi et al. | 600/10 |
| 5,150,712 A | 9/1992 | Dory | 128/660 |
| 5,158,536 A | 10/1992 | Sekins et al. | 604/20 |
| 5,193,526 A * | 3/1993 | Daikuzono | 128/7 |
| 5,209,748 A * | 5/1993 | Daikuzono | 606/16 |
| 5,217,455 A * | 6/1993 | Tan | 606/9 |
| 5,222,953 A | 6/1993 | Dowlatshahi | 606/15 |
| 5,226,907 A | 7/1993 | Tankovich | |
| 5,290,273 A * | 3/1994 | Tan | 606/9 |
| 5,429,582 A | 7/1995 | Williams | 600/2 |
| 5,445,608 A * | 8/1995 | Chen et al. | 604/20 |
| 5,540,737 A | 7/1996 | Fenn | 607/101 |
| 5,541,947 A | 7/1996 | Mourou et al. | 372/25 |
| 5,549,596 A * | 8/1996 | Latina | 606/4 |

(Continued)

FOREIGN PATENT DOCUMENTS

EP     0649667 A2 *     4/1995

(Continued)

OTHER PUBLICATIONS

International Search Report for application No. PCT/US99/17176, dated Oct. 25, 1999.

(Continued)

*Primary Examiner*—Thomas Barrett
(74) *Attorney, Agent, or Firm*—Cook, Alex, McFarron, Manzo, Cummings & Mehler, Ltd.

(57) ABSTRACT

A method and apparatus for selectively photobleaching or killing pigmented tissues by photochemically converting pigments in the tissues using light and specifically two-photon excitation. Phototoxic products thereby produced then kill pigmented cells. Hyperthermia or an exogenous agent can also be added to augment efficacy. The present invention is also directed to selective thermal destruction of pigmented tissues using related optical means.

68 Claims, 10 Drawing Sheets

U.S. PATENT DOCUMENTS

| | | | | |
|---|---|---|---|---|
| 5,571,152 | A | * | 11/1996 | Chen et al. ............... 607/92 |
| 5,586,981 | A | * | 12/1996 | Hu ............................. 606/9 |
| 5,620,479 | A | | 4/1997 | Diederich ................. 607/97 |
| 5,647,866 | A | | 7/1997 | Zaias et al. |
| 5,656,186 | A | * | 8/1997 | Mourou et al. ......... 219/121.69 |
| 5,669,916 | A | | 9/1997 | Anderson |
| 5,707,401 | A | * | 1/1998 | Talmore .................. 607/88 |
| 5,720,894 | A | | 2/1998 | Neev et al. ............... 216/65 |
| 5,735,844 | A | | 4/1998 | Anderson et al. ........ 606/9 |
| 5,775,339 | A | * | 7/1998 | Woodburn et al. ...... 128/898 |
| 5,829,448 | A | | 11/1998 | Fisher et al. ............. 128/898 |
| 5,860,967 | A | | 1/1999 | Zavislan et al. .......... 606/9 |
| 5,952,818 | A | | 9/1999 | Zhang et al. ............. 324/96 |
| 5,957,960 | A | * | 9/1999 | Chen et al. ............... 607/92 |
| 6,099,522 | A | | 8/2000 | Knopp et al. ............ 606/10 |
| 6,331,286 | B1 | | 12/2001 | Dees et al. |

FOREIGN PATENT DOCUMENTS

| | | |
|---|---|---|
| EP | 0 649 677 B1 | 2/2001 |
| WO | WO 96/07431 | 3/1996 |
| WO | WO 97/03697 | 2/1997 |
| WO | WO 97/26920 | 7/1997 |
| WO | WO 98/18399 | 5/1998 |

OTHER PUBLICATIONS

Stables, G.I. et al, "Photodynamic Therapy, Antitumour Treatment," *Cancer Treatment Reviews*, vol. 21, pp. 311-323, 1995.

Katsumi, T.A. et al, "Photodynamic Therapy with a Diode Laser for Implanted Fibrosarcoma in Mice Employing Mono-L-Aspartyl Chlorin $E_6$," *Photochemistry and Photobiology*, vol. 64, No. 4, pp. 671-675, 1996.

de Vries et al, "Increased susceptability to ultraviolet-B and carcinogens of mice lacking the DNA excision repair gene XPA," Nature,377; 169-173; 1995.

Sands et al, "High susceptibility to ultraviolet-induced carcinogenesis in mice lacking XPC," Nature, 377; 162-165, 1995.

Nakane et al, "High incidence of ultraviolet-B- or chemical-carcinogen-induced skin tumors in mice lacking the xenoderma pigmentosum group A gene," Nature, 377; 165-168, 1995.

Watanabe et al, "Comparative studies of femtosecond to microsecond laser pulses on selective pigmented cell injury in skin," Photochem. Photobiol., 53, 757-762, 1991.

Anderson et al, "Selective photothermolysis of cutaneous pigmentation by Q-switched Nd:YAG laser pulses at 1064, 532 and 355 nm," J. Invest. Dermatol., 93; 28-32, 1989.

Ahmed, I., "Malignant melanoma," Mayo Clinic Proced., 72; 356-361, 1997.

Hadjur et al, "Photodynamic effects of hypericin on lipid peroxidation and antioxidant status in melanoma cells," Photochem. Photobiol., 64; 375-381, 1996.

Roger et al, "Mucosal, genital and unusual variants of melanoma," Mayo Clinic Proced., 72; 362-366, 1977.

Rigel, D.S., "Malignant melanoma: incidence issues and their effect on diagnosis and treatment," Mayo Clinic Proced., 72; 367-371, 1997.

Riley, P.A., "Melanin," Int. J. Biochem., Cell Biol., 29; 1235-1239, 1997.

Schmitz et al, "Dual role of melanins and melanin precursors as photoprotective and phototoxic agents: inhibition of ultraviolet radiation-induced lipid peroxidation," Photochem. Photobiol., 61; 650-655, 1995.

Young, A.R., "Chromophores in human skin," Phys. Med. Biol., 42; 789-802, 1997.

Swofford, R.L. and W.M. McClaim, (1975) The effect of saptial and temporal laser beam characteristics on two-photon absorption. Chem. Phys. Lett. 3 4, 455-459.

Shea C.R., et al., (1990) Mechanistic investigation of doxycyckine photosensitization by picosecond-pulsed and continuous wave laser irradiation of cells in culture. J. Biol. Chem. 2 6 5, 5977-5982.

Inaba, H., et al., (1985) Nd:YAG laser-induced hematoporphyrin visible flourescence and two-photon-excited photochemical effect on malignant tumor cells. J. Opt. Soc. Am. A:Opt. Inage Science 2, P72 (mtg abstr).

Mashiko, S., et al., (1986) Two-photon excited visible flourescence of hematoporphyrin and phiophorbide a and in vitro experiments of the photodynamic . . . J. Opt. Soc. Am. B:Opt. Phys 3, P72-P73 (mtg. abstr).

Steil, H., et al., (1993) Photophysical properties of the photosensitizer phophorbide a studied at high photon flux densities. J. Photochem. Photobiol. B: Biology 1 7,181-186.

Bodaness, R.S. and D.S. King (1985) The two-photon induced flourescence of the tumor localizing photosensitizer hematoporphyrin derivative via 1064 nm . . . Biochem. Biophys. Res. Comm. 1 2 6, 346-351.

Bodaness, R.S., et al., (1986) Two-photon laser-induced fluorescence of the tumor-localizing photosensitive hematoporphyrin derivative. J. Biol. Chem. 2 6 1, 12098-12101.

Lenz, P., (1995) In vivo excitation photosensitizers by infrared light. Photochem. Photobiol. 6 2, 333-338.

Patrice, T., et al., (1983) Neodymium-yttrium aluminum gamet laser destruction of nonsensitized and hematoporphyrin derivative-sensitized tumors. Canc. Res. 4 3, 2876-2879.

Marchesini, R., et al., (1986) A study on the possible involvement of nonlinear mechanism of light absorption by HpD with Nd:YAG laser. Lasers Surg. Med. 6, 323-327.

Oh, D.H., et al., (1997) Two-photon excitation of 4'-hydroxymethyl-4,5', 8-trimethylpsoralen. Photochem. Photobiol. 6 5, 91-95.

McClain, W.M., (1974) Two-photon molecular spectroscopy. Acc. Chem. Res. 7, 129-135.

Zhu, Ning Wen, et al., (1997) Sub-Lethal Effects of Exposing The Human Melanoma Cell Line SKmel-23 to 532 nm Laser Light. Int. J. Cancer: 72, 1104-1112.

Sitnik, Theresa M. et al. (1998) The Effect of Fluence Rate on Tumor and Normal Tissue Responses to Photodynamic Therapy. Photochemistry and Photobiology, pp. 462-466.

M.J. Wirth, et al., "Two-Photon Excited Molecular Fluorescence in Optically Dense Media," Analytical Chemistry, 49(1977) 2054-2057.

Cheong, W-F. et al., "A Review of the Optical Properties of Biological Tissues" IEEE 5. Quant. Election 2 6, 2166-2185 (1990).

Göpert-Mayer, M., (1931) Elementary process with two quantum jumps. Ann. Physik 9, 273-294.

Kaiser, W. and C.G.B. Garrett, (1961) Two photon excitation in $CaF_2:Eu^{2+}$. Phys. Rev. Lett. 7, 229-231.

Monson, P.R. and W.M. McClain (1970) Polarization dependence of the two-photon absorption of tumbling molecules with application of liquid 1-choronaphthalene and benzene. J. Chem. Phys. 5 3, 29-37.

Draumer, N.H., et al., (1997) Femtosecond dynamics of excited-state evolution in $[Ru(bpy)^3]^{2+}$. Science 2 7 5, 54-57.

de Vries et al, "Increased susceptability to ultraviolet-B and carcinogens of mice lacking the DNA excision repair gene XPA," Nature, 377; 169-173; 1995.

Sands et al, "High susceptibility to ultraviolet-induced carcingenesis in mice lacking XPC," Nature, 377; 162-165, 1995.

Nakane et al, "High incidence of ultraviolet-B- or chemical-carcinogen-induced skin tumors in mice lacking the xenoderma pigmentosum group A gene," Nature, 377; 165-168, 1995.

Watanabe et al, "Comparative studies of femtosecond to microsecond laser pulses on selective pigmented cell injury in skin," Photochem. Photobiol., 53, 757-762, 1991.

Anderson et al, "Selective photothermolysis of cutaneous pigmentation by Q-switched Nd:YAG laser pulses at 1064, 532 and 355 nm," J. Invest. Dermatol., 93; 28-32, 1989.

Ahmed, I., "Malignant melanoma," Mayo Clinic Proced., 72; 356-361, 1997.

Favilla et al., "Photodynamic therapy: a 5 year study of its effectiveness in the treatment of posterior uveal melanoma and evaluation of haematoprophyrin uptake and phototoxicity of melanoma cells in tissue culture," Melanoma Res., 5; 355-364, 1995.

Hadjur et al, "Photodynamic effects of hypericin on lipid peroxidation and antioxidant status in melanoma cells," Photochem. Photobiol., 64; 375-381, 1996.

Roger et al, "Mucosal, genital and unusual variants of melanoma," Mayo Clinic Proced., 72; 362-366, 1977.

Rigel, D.S., "Malignant melanoma: incidence issues and their effect on diagnosis and treatment," Mayo Clinic Proced, 72; 367-371, 1997.

Riley, P.A., "Melanin," Int. J. Biochem., Cell Biol., 29; 1235-1239, 1997.

Schmitz et al, "Dual role of melanins and melanin precursors as photoprotective and phototoxic agents: inhibition of ultraviolet radiation-induced lipid peroxidation," Photochem. Photobiol., 61; 650-655, 1995.

Young, A.R., "Chromophores in human skin," Phys. Med. Biol., 42; 789-802, 1997.

Swofford, R.L. and W.M. McClaim, (1975) The effect of saptial and temporal laser beam characteristics on two-photon absorption. Chem. Phys. Lett. 3 4, 455-459.

Shea C.R., et al., (1990) Mechanistic investigation of doxycyckine photosensitization by picosecond-pulsed and continuous wave laser irradiation of cells in culture. J. Biol. Chem. 2 6 5, 5977-5982.

Inaba, H., et al., (1985) Nd:YAG laser-induced hematoporphyrin visible flourescence and two-photon-excited photochemical effect on malignant tumor cells. J. Opt. Soc. Am. A:Opt. Inage Science 2, P72 (mtg abstr).

Mashiko, S., et al., (1986) Two-photon excited visible flourescence of hematoporphyrin and phiophorbide a and in vitro experiments of the photodynamic . . . J. Opt. Soc. Am. B:Opt. Phys 3, P72-P73 (mtg. abstr).

Steil, H., et al., (1993) Photophysical properties of the photosensitizer phophorbide a studied at high photon flux densities. J. Photochem. Photobiol. B: Biology 1 7, 181-186.

Bodaness, R.S. and D.S. King (1985) The two-photon induced flourescence of the tumor localizing photo-sensitizer hematoporphyrin derivative via 1064 nm . . . Biochem. Biophys. Res. Comm. 1 2 6, 346-351.

Bodaness, R.S., et al., (1986) Two-photon laser-induced fluorescence of the tumor-localizing photosensitive hematoporphyrin derivative. J. Biol. Chem. 2 6 1, 12098-12101.

Lenz, P., (1995) In vivo excitation of photosensitizers by infrared light. Photochem. Photobiol. 6 2, 333-338.

Patrice, T., et al., (1983) Neodymium-yttrium aluminum gamet laser destruction of nonsensitized and hematoporphyrin derivative-sensitized tumors. Canc. Res. 4 3, 2876-2879.

Marchesini, R., et al., (1986) A study on the possible involvement of nonlinear mechanism of light absorption by HpD with Nd:YAG laser. Lasers Surg. Med. 6, 323-327.

Oh, D.H., et al., (1997) Two-photon excitation of 4'-hydroxymethyl-4,5', 8-trimethylpsoralen. Photochem. Photobiol. 6 5, 91-95.

McClain, W.M., (1974) Two-photon molecular spectroscopy. Acc. Chem. Res. 7, 129-135.

Dees et al. "Treatment of Murine Cutaneous Melanoma with Near Infrared Light" Photochemistry and Photobiology, 2002, pp. 296-301.

Communication from EPO regarding European Patent Application No. 99940828, Mailed Feb. 2, 2005. Includes European Search Report.

Xanthenes: Fluorone Derivatives, The Journal Of Organic Chemistry 57(1992) Jul. 31, No. 16, Washington, DC pps 4418-4421.

(Svensk Farmaceutisk Tidskrift (1973) 77 (13): 641-647 (Abstract).

* cited by examiner

TREATMENT OF PIGMENTED TISSUES USING OPTICAL ENERGY

This is a continuation-in-part of U.S. patent application Ser. No. 08/739,801, filed on Oct. 30, 1996, now U.S. Pat. No. 5,829,448-Nov. 3, 1998 entitled "Method for Improved Selectivity In Photoactivation of Molecular Agents".

BACKGROUND OF THE INVENTION

The present invention is directed to a method and apparatus for treating pigmented tissues by selective photoactivation of pigments in such tissues using optical energy and more specifically two-photon excitation. This selective photoactivation may be used to effect photobleaching of such pigments or to effect photochemical conversion of such pigments into phototoxic products. Photobleaching reduces or eliminates undesirable pigmentation, for example that caused by pigments present in moles, freckles, hair follicles and tattoos. Photochemical conversion produces phototoxic products that destroy pigmented tissues, such as those pigmented tissues in pigmented tumors. The present invention is also directed to selective thermal destruction of pigmented tissues using related optical means.

Photobleaching is the transient or permanent reduction of pigmentation in pigmented tissues upon optical illumination, typically occurring during intense illumination with visible or ultraviolet light. Photobleaching occurs when photoactive pigments are photochemically transformed from a highly colored state to a less highly colored state (de-pigmentation). For example, photobleaching may be used to reduce or eliminate undesirable pigmentation present in moles and hair follicles or to destroy dyes present in tattoos. It is desired that treated tissues will exhibit localized de-pigmentation without side effects, such as irritation or cell necrosis. However, previous methods for photobleaching tissues using visible or ultraviolet light have produced undesirable collateral effects, including irritation of surrounding tissues and possible scarring at the treatment site.

In contrast to photobleaching, photochemical conversion of pigments into phototoxic products involves stimulation of localized cell necrosis in treated tissues. This is also effected by optical illumination, typically occurring when intense visible or ultraviolet light is used to illuminated susceptible pigmented tissues. Such localized necrosis may be useful for selective destruction of diseased tissues, such as those present in tumors or benign skin lesions.

More specifically, an important subset of pigmented tissues are pigmented tumors, such as melanomas, which are life threatening and highly difficult to treat. While melanomas can be treated if detected early using standard surgical, radiation or chemotherapeutic methods, these methods still do not have acceptable levels of effectiveness and produce high levels of collateral damage to normal tissue. Hence, even if detected relatively early, the prognosis is usually poor.

Further, if a melanoma has metastasized beyond the primary tumor site, less than 20% of patients will survive beyond five years. For such melanomas, there are no effective therapies. Patients diagnosed with such a metastatic melanoma will survive on average only 3–6 months after the diagnosis even with therapeutic intervention.

Further exacerbating the difficulties in treating melanomas is the fact that the incidence of melanoma in Caucasians is increasing at a rate of 6% per year. This is currently the second fastest rate of increase in cancer occurrences—second only to tobacco related cancers of the lung in women. Currently, the lifetime risk of melanoma in the U.S. is 1 in 75. Accordingly, new effective therapeutic modalities are required to treat both primary and metastatic pigmented tumors such as melanomas.

One possible approach for treating pigmented tissues involves the use of melanins, their precursors, and other endogenous or exogenous pigments.

More specifically, there are several pigments in humans that are collectively known as melanins. The function of melanins are to protect tissues from the deleterious effects of electromagnetic radiation (e.g. light). However, melanins and their precursors can also be converted to phototoxic products. For example, a melanin precursor (5-SCD) has been shown to photobind to DNA after exposure to 300 nm (ultraviolet light) illumination. Further, 5-SCD has been shown to be chemically unstable in the presence of ultraviolet (UV) illumination and oxygen, thereby suggesting that phototoxic products of the (1) Type I variety (phototoxic) or the (2) Type II variety (photocatalytic) may be produced.

Additionally, many melanoma cells are amelanotic. These cells produce melanin precursors but only small quantities of melanin. Phototoxic damage (induction of single strand breaks) to DNA by at least two precursors to melanin (5-SCD and DIHCA) has been demonstrated upon exposure to UV light. Amelanotic cells will be killed by photodynamic therapy (PDT) performed on such precursors to melanin (e.g., 5-SCD, DIHEA). Thus, melanomas can be killed by delivering energy via light.

However, utilization of such phototoxic reactions by illumination of melanin, melanin precursors, or other endogenous pigments has not previously been possible. The UV/Near UV light required for photoactivation is unable to penetrate into normal or cancerous skin (i.e. beyond 2–3 mm.) More specifically, the poor penetration of such light has produced little effect on patients whose skin tumors are larger than or at a depth greater than 3 mm. As a result, only 40–50% of patients whose tumors exceed 3 mm will survive. Accordingly, the survival rate of melanoma patients with tumors whose depth is less than 1 mm is drastically better than those who have tumors which are either located at a depth of greater than 3 mm or extend to a depth greater than 3 mm.

Previous photodynamic methods using UV/Near UV light also produced undesirable collateral effects that not only prohibited the photoconversion of melanin and prevented it from killing pigmented tissues but also was potentially dangerous to the patient. For example, UV light can create thymidine dimers which damage genetic material. DNA damage is a major and possibly the sole cause of skin cancers like melanomas. Melanin's absorbance of UV light is designed to prevent this from happening. However, UV light, chemotherapy, and ionizing radiation have recently been shown to increase the virulence of tumor cells. As a result, tumor cells when treated with UV light will have a greater mutation and error rate because the UV light can inactivate mechanisms designed to identify and correct genetic errors (in addition to creating new errors). Therefore, prior techniques were not only unable to effectively kill pigmented tissues by accessing endogenous pigments but also created side effects that could be lethal.

In many instances, the effectiveness of various photodynamic processes have been found to be markedly increased by simultaneous photoactivation and localized heating (hyperthermia). Typically, by heating the treatment zone 2–10° C. above normal temperatures, the effectiveness of PDT is increased many fold. Such heating alone, however, has not been shown to produce a significant therapeutic effect. In contrast, the inventors of the present invention have conceived that more acute localized heating (i.e., >2–10° C. temperature rise) of tissues and tissue components within the treatment zone may produce a therapeutic effect by causing thermal overload in the treated tissues.

Therefore, it is an object of the present invention to provide a method for accessing endogenous pigments in pigmented tissues so as to be able to selectively photobleach said pigments.

It is another object of the present invention to provide a method for accessing endogenous pigments in pigmented tissues so as to be able to photochemically convert said pigments into phototoxic products.

It is another object of the present invention to provide a method that will access said endogenous pigments in pigmented tissues without accessing endogenous pigments in healthy tissues surrounding said pigmented tissues.

It is another object of the present invention to provide a method that will augment the effectiveness of said photochemical conversion of said endogenous pigments in said pigmented tissues through the localized application of hyperthermia in said pigmented tissues.

It is another object of the present invention to provide a method that will photothermally destroy pigmented tissues without harming healthy tissues surrounding said pigmented tissues.

SUMMARY OF THE INVENTION

The present invention is directed to a method and apparatus for treatment of a particular volume of tissue or material containing an endogenous pigment. In general, typically, the present invention uses the unique properties of simultaneous two-photon excitation with endogenous pigment in a particular volume of tissue, such as a tumor, to selectively photoactivate the pigment.

This photoactivated pigment may thereby be photobleached or photochemically converted into a phototoxic product. Such photoactivation results from the simultaneous two-photon excitation of the pigment. Preferably, the photons responsible for photoactivation are provided by a laser which produces a beam of light comprising a train of one or more ultrashort pulses. This beam of light can be a focused beam of light if the location and extent of the particular volume of tissue to be treated is precisely known. The focused beam of light can then be scanned throughout the volume of the tissue to treat the entirety of the pigmented tissue. Alternatively, where the location and extent of the pigmented tissue in a volume of tissue is not precisely known, a non-focused light beam can be used.

In an alternative embodiment, an exogenous photodynamic agent can be added to the particular volume of tissue. The exogenous agent can be photoactivated by the simultaneous two-photon excitation. Activation of the exogenous photodynamic agent augments the effectiveness of the endogenous pigment.

In a further alternate embodiment of the invention, the effectiveness of such photoactivation is augmented through the localized application of hyperthermia in the pigmented tissues.

In an additional further alternative embodiment of the invention, the particular volume of tissue is treated with light to promote thermal overload of the pigmented tissues. Thermal overload heats and kills the pigmented tissues.

BRIEF DESCRIPTION OF THE DRAWINGS

In describing the preferred embodiments, reference is made to the accompanying drawings.

DETAILED DESCRIPTION OF THE PRESENTLY PREFERRED EMBODIMENT

The present invention is directed to a method and apparatus for treating pigmented tissues using light. Such treatment includes the following photochemical outcomes of therapeutic value: (1) the elimination of undesirable pigmentation in pigmented tissues through photobleaching; and (2) the permanent destruction of pigmented tissues through photochemical conversion of pigments into phototoxic products. More specifically, simultaneous two-photon excitation is used to photochemically convert endogenous or exogenous pigments into desired photoactive products, resulting in the desired photobleaching or tissue destruction. Photobleaching is used to reduce or eliminate undesirable coloration of tissue, such as that in moles, freckles, hair follicles and tattoos. The production of phototoxic products may be used to preferentially kill pigmented tumor cells or other undesirable tissues while sparing normal cells. Significantly, the methods and apparatus in the present invention used for photobleaching and production of phototoxic products utilize equivalent photoactivation mechanisms, differing substantially only in the intended treatment target.

In the preferred embodiment, the present invention uses simultaneous two-photon excitation to photoactivate pigments in the pigmented tissues, yielding photobleached or phototoxic products.

In an alternate preferred embodiment, the present invention uses related optical means to selectively destroy pigmented tissues via photothermal means.

Simultaneous Two Photon Excitation

"Simultaneous two-photon excitation" is the non-linear optical excitation occurring as a result of the essentially simultaneous interaction of two photons originating from a single ultrashort laser pulse with one or more agents or pigments to produce one or more photoactivated agents or pigments. "Non-linear optical excitation" means those excitation processes involving the essentially simultaneous interaction of two photons with one or more agents or pigments. "Essentially simultaneous interaction" means those excitation processes occurring as a result of the interaction of one or more agents or pigments with photons provided by a single ultrashort laser pulse. Ultrashort means less than approximately 10 ns.

Figure 1:
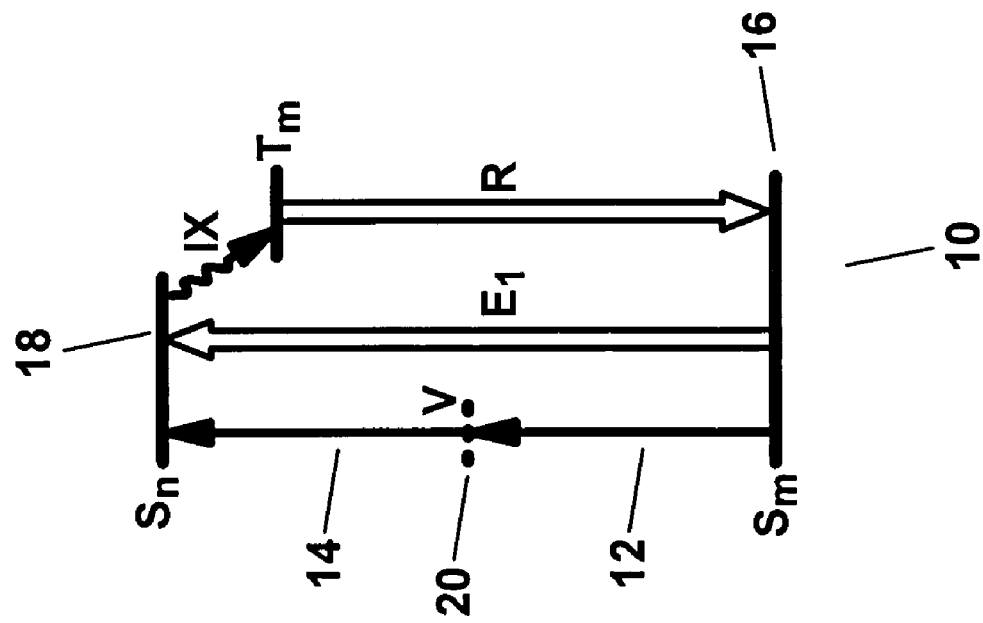
FIG. 1 illustrates an example energy level diagram for simultaneous two-photon excitation.

As shown in FIG. 1, simultaneous two-photon excitation to an allowed energy level 10 occurs when a photoactive agent is excited from a first allowed electronic energy level 16 upon absorption of a certain energy $E_1$ that is provided by the simultaneous, combined interaction of two photons 12 and 14 with the agent. If the energies of both photons 12 and 14 are identical, the excitation process is termed "degenerate". The simultaneous interaction of the two photons is frequently described as being mediated by a transient virtual state 20 with a lifetime on the order of 10 femtoseconds (fs) or less. If both photons do not interact with the agent during this lifetime, excitation does not occur and the agent fails to reach the excited state $S_n$ (18). Typically, intersystem crossing, IX, subsequently occurs to bring the excited agent to a long-lived activated state $T_m$ from which a photochemical reaction R can occur.

Simultaneous two-photon excitation may thereby be used to excite processes that normally occur upon absorption of a single UV or visible photon through the simultaneous absorption of two near-infrared photons.

An example of the simultaneous two-photon excitation process is the promotion of melanin precursors from a ground electronic state to an excited electronic state through the simultaneous absorption of two photons at 600 nm, followed by binding of the excited melanin precursor to DNA (this is conventionally excited using a single photon at 300 nm). In this example, the probability of excitation is related to the product of the instantaneous or peak powers of the first of two photons 12 and the second of two photons 14. This can be conceptualized in the form of a photochemical reaction,

$$\text{Molecule}_{GROUND\ STATE} + 2h\nu_{600\ nm} \rightarrow \text{Molecule}_{EXCITED\ STATE} \qquad (1)$$

which shows that a molecule in the ground state is promoted to an excited state following simultaneous absorption of two photons at 600 nm, $h\nu_{600\ nm}$. The reaction rate R, is given by $R = k[\text{Molecule}_{GROUND\ STATE}] [h\nu_{600\ nm}]^2$, where k is a rate constant and where $[\text{Molecule}_{GROUND\ STATE}]$ and $[h\nu_{600\ nm}]$ symbolize concentrations of ground state molecules and excitation photons, respectively. Hence, due to the well known quadratic dependence on instantaneous photon irradiance, simultaneous two-photon excitation to an allowed energy level 10 is also referred to as a non-linear excitation process.

A more detailed explanation of simultaneous two-photon excitation and other non-linear and linear processes is described in U.S. patent application Ser. No. 08/739,801 filed Oct. 30, 1996 for "Method For Improved Selectivity In Photoactivation Of Molecular Agents" assigned to the same assignee of the present application and which is incorporated herein by reference.

Significance of Absorbance and Scattering Properties in Single-Photon and Simultaneous Two-Photon Processes:

While the cross-section for simultaneous two-photon excitation may be considerably lower than that observed with single-photon excitation, use of the simultaneous two-photon excitation in the present invention may be favorable over single-photon excitation under many conditions because of lower matrix absorption and optical scattering of longer wavelength optical radiation. For example, FIG. 2 shows the absorption and scattering properties for various components of animal tissue, such as human dermis, covering the ultraviolet (UV) to near infrared (NIR) spectral region.

Figure 2:
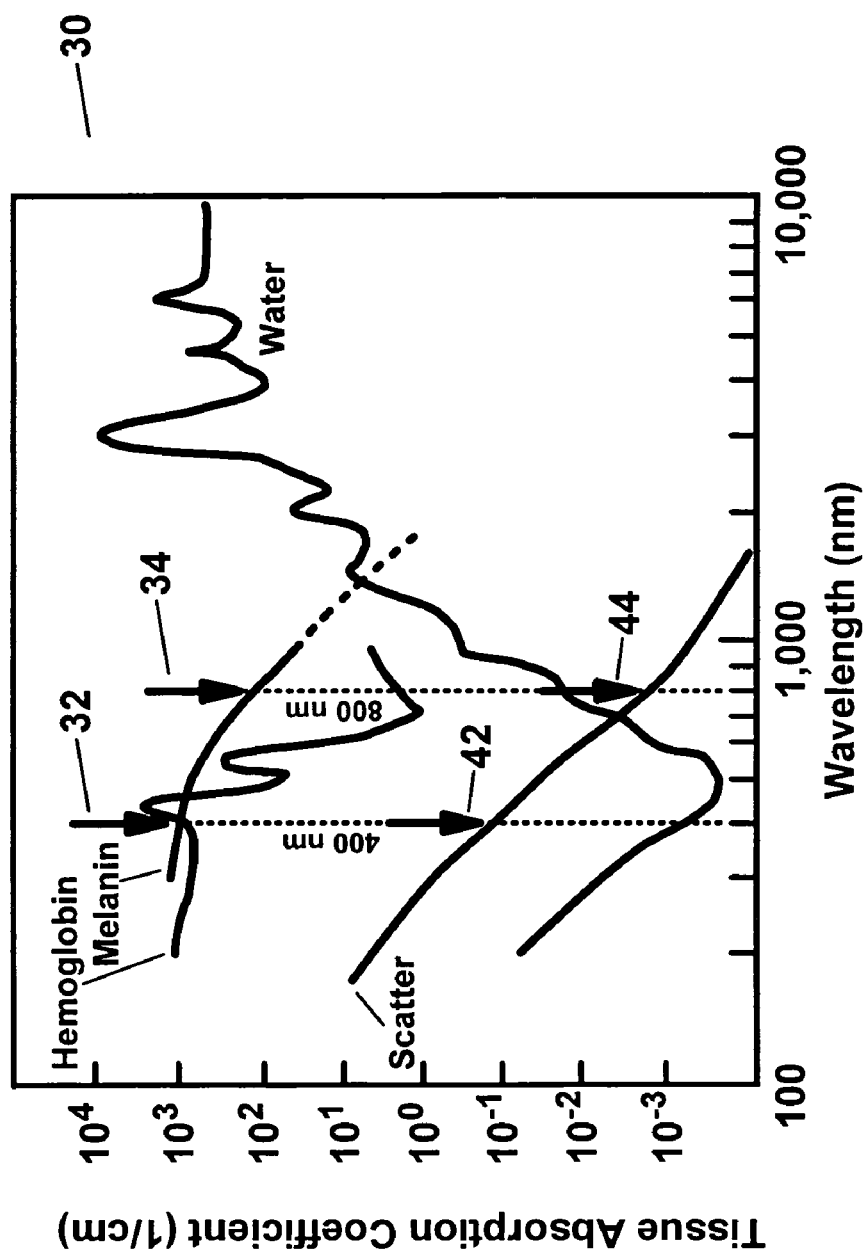
FIG. 2 illustrates an example of absorption and scattering properties for animal tissue covering the ultraviolet to infrared spectral region.

Specifically, FIG. 2 demonstrates how higher-energy photons 32 may experience considerably greater tissue absorption than lower-energy photons 34. For example, human skin strongly absorbs higher-energy photons 32 at 400 nm, but is relatively transparent to lower-energy photons 34 at 800 nm. This is a consequence of the natural absorbance of higher-energy photons 32 by blood, pigments, proteins, and genetic materials, among other natural components, of skin.

FIG. 2 further demonstrates how higher-energy photons 42 may experience considerably greater tissue scatter than lower-energy photons 44. Any optically dense medium, such as human skin, will strongly scatter higher-energy photons 42, for example at 400 nm, but will exhibit much lower scatter for lower-energy photons 44 at 800 nm.

These differences in optical properties have two important consequences. First, absorption of short-wavelength, higher-energy photons 32 by tissue can result in undesirable tissue damage upon exposure to UV or other high-energy light. In contrast, negligible effects may be experienced upon illumination with lower-energy photons 34, such as NIR light, even when the optical power of the NIR light is many-fold higher than that of the UV light. Secondly, the inherently high absorption and scatter of higher-energy photons 32 by tissue can result in very shallow tissue penetration depths, while lower-energy photons 34 generally have much greater penetration depths.

Figure 3:
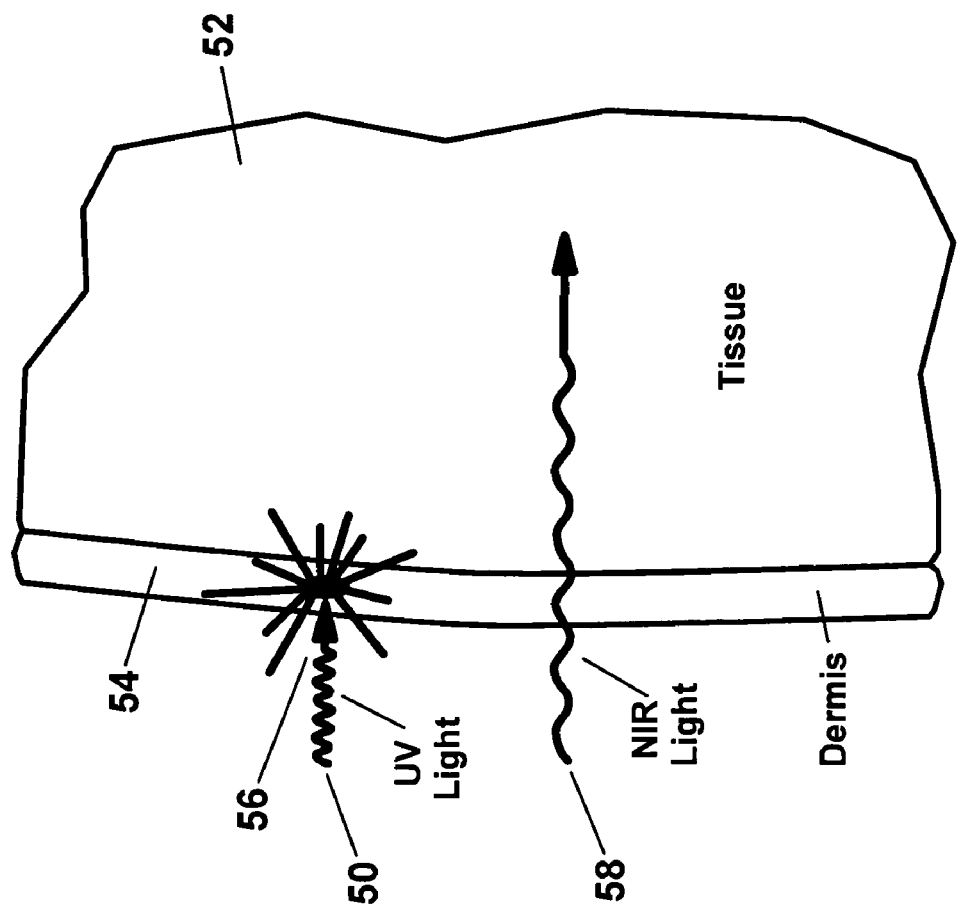
FIG. 3 shows the general trends in optical absorption properties of animal tissue for short wavelength and long wavelength light.

These important differences in absorption and penetration depth properties for higher-energy and lower-energy light are shown schematically in FIG. 3. When UV light 50, for example light at 400 nm, impinges on human tissue 52, the majority of the optical energy is immediately absorbed and scattered in the outermost layers 54, such as the epidermis and dermis. Absorption may occur due to excitation of certain molecules in the cells of these outermost layers 54, such as those composing the genetic material in the cellular nucleus. This absorption of higher-energy light by cellular constituents can thereby initiate a variety of collateral photochemical changes 56 in these cells. These collateral photochemical changes 56 resulting from absorption of UV light 50 can include irreversible genetic damage and induction of cancer.

In contrast, NIR light 58, for example at 800 nm, will not be appreciably absorbed or scattered by tissue 52 or its outermost layers 54. The overall depth of penetration will be much greater, and the extent of collateral damage to cells will be substantially lower. Hence, if long-wavelength excitation light is used to replace the higher-energy light used for conventional single-photon excitation, it is possible to photoactivate specific molecules or pigments using relatively non-damaging, high penetration depth, simultaneous two-photon excitation.

Figure 4:
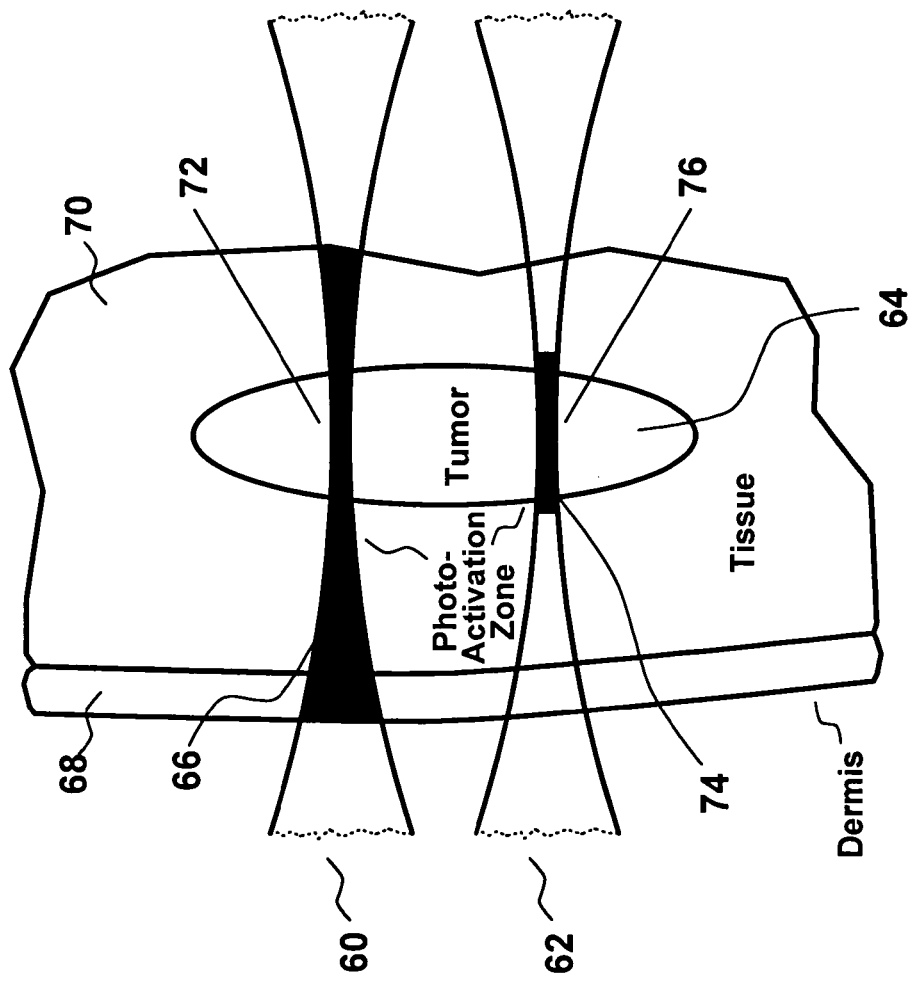
FIG. 4 illustrates a comparison of optical activation in tissue when single-photon and two-photon excitation methods are used.

Furthermore, the properties of simultaneous two-photon excitation have additional implications when coupled with the inherent non-damaging nature and low absorption of NIR light. For example, FIG. 4 compares the extent of optically-induced damage in tissue when single-photon excitation 60 and simultaneous two-photon NIR excitation 62 methods are used to illuminate a subcutaneous tumor 64.

Single-photon excitation 60 produces a photoactivation zone 66 that extends substantially along the entire optical path and has no significant biospecificity. Hence, in addition to induction of the desired photoactivation in the tumor 64, collateral damage can occur throughout surrounding tissues, such as the dermis 68 and surrounding healthy tissue 70. If the single-photon excitation 60 is focussed, the photoactivation zone 66 will be slightly enhanced at the focus 72. This photoactivation zone 66, however, might not even extend into the tumor 64 if the UV or visible light is absorbed by the epidermis, dermis 68 or surrounding healthy tissue 70 prior to reaching the tumor 64. This can occur as a consequence of the inherently high absorptivity of tissue at short wavelengths.

In contrast, use of NIR light for simultaneous two-photon excitation 62 produces a sharply defined remote photoactivation zone 74 that is spatially localized at the focus 76 as a consequence of the non-linear properties of this excitation method. Such localization of activation in such a focal zone is a unique property of non-linear excitation processes, such as two-photon excitation. Furthermore, because tissue does not appreciably absorb NIR light, collateral damage to the surrounding dermis 68 and healthy tissue 70 is minimized.

Therapeutic Applications of Simultaneous Two-Photon Excitation:

The foregoing discussion suggests that the fundamental differences in the absorption of UV and NIR light by tissue and cellular constituents, coupled with the special non-linear properties of simultaneous two-photon excitation, have direct applicability for improvements in various medical treatments, specifically in the modification or elimination of pigmented tissues.

Such simultaneous two-photon excitation enables improved localization in the photoactivation of photoactive agents with significantly reduced potential for collateral tissue damage compared with that possible using conventional methods.

Where control of penetration is not critical, non-focussed NIR light may be used to stimulate simultaneous two-photon photoactivation of agents present in a relatively large illuminated area. In such a case, the extent of agent photoactivation is controlled by varying the location, intensity and duration of exposure of such agents to the NIR beam.

Where precise control of penetration depth or volume extent of therapeutic application is more critical, focussed NIR light may be used to stimulate the simultaneous two-photon photoactivation process. In such a case, beam irradiance, exposure duration, and degree of focussing are used to control the extent of agent photoactivation.

In both cases, high-irradiance NIR light may be used to achieve maximum efficacy. Furthermore, the high penetration depths achievable with NIR light combined with the inherent localization of photoactivation that is possible with focused simultaneous two-photon excitation provide a means for photoactivating agents in subsurface tissues without damaging overlying or underlying healthy tissues.

Simultaneous Two-Photon Treatment with Endogenous Pigments

The method of the present invention improves on the above-described advantages through the use of simultaneous two-photon excitation to produce a therapeutic outcome based on photoactivation of endogenous pigments in order to treat pigmented tissues. "Endogenous" means pre-existing in a patient or target. "Pigments" means naturally occurring agents that absorb optical energy. Examples of such pigments include melanin, melanin precursors, carotenes, porphyrins (such as hemoglobin), various tattoo dyes and other optically active species. "Therapeutic outcome" means photobleaching or photodynamic destruction of treated pigmented tissues resulting from the natural biological action of a photoactivated endogenous pigment. "Photobleaching" is the reduction or elimination of undesirable pigmentation, for example that caused by endogenous pigments present in moles, freckles, hair follicles and tattoos. "Photodynamic destruction" is localized tissue necrosis resulting from photochemical production of phototoxic products that destroy pigmented tissues, such as those pigmented tissues in pigmented tumors. Tissues suitable for treatment include pigmented tissues in which a specific therapeutic outcome is desired, such as moles, freckles, pigmented tumors, benign lesions, hair follicles and tattoos.

In a further embodiment of the present invention, a precursor to the endogenous pigments may be used. Examples of such precursors to pigments include 5-S-cysteinyldopa (5-SCD) and 5,6-dihydroxyindole (DHI), dopa, dopa semiquinone, leucodopachrome, dopachrome, eumalanins, pheomelanins, sepia melanins, and 5,6-dihydroxyindole-2-carboxylic acid. Such precursors have both photoprotective and phototoxic abilities. A metabolic precursor to melanin is a biochemical (e.g. 5-SCD, DHI) that is produced by the cell as part of the synthetic pathway that produces melanin. Melanin precursors, when activated by light, can generate phototoxic products that damage cellular materials (e.g., DNA) killing the target cells. Melanin precursors can be activated by two-photon excitation, as explained supra.

As also explained supra, melanin, melanin precursors, and other endogenous pigments are naturally occurring in human tissue, including in tumors. Such melanins, melanin precursors, or other endogenous pigments can be converted to phototoxic products after exposure to light.

The present invention uses the above-described simultaneous two-photon excitation to specifically target melanin, melanin precursors, or other endogenous pigments in pigmented tissues (such as melanomas and other tumors). The pigment is converted to a phototoxic product by NIR light upon simultaneous two-photon excitation. The phototoxic product then causes damage to the pigmented tissues (by for example photobinding to cellular DNA or causing breaks in this DNA). This kills the cells in the pigmented tissues and, therefore, destroys it. Because simultaneous two-photon excitation is used to specifically target the melanin, melanin precursors, or other endogenous pigments only in the targeted tissue, any melanin, melanin precursors, or other endogenous pigments in the tissue surrounding the targeted tissue are not converted to phototoxic products.

More specifically, use of simultaneous two-photon excitation produces a sharply defined focal zone that is substantially localized in depth and cross-section. This focal zone can be localized to the targeted tissue (such as a tumor) to be killed or a small zone within or surrounding this tissue. As a result, photoactivation will only occur in the focal zone (i.e. in the tumor). Hence, any melanin, melanin precursors, or other endogenous pigment not in the targeted tissue, such as for example, in tissue surrounding a tumor, will not be photoactivated because it is outside the focal zone.

Additionally, as explained supra, the simultaneous two-photon excitation is able to penetrate deep into normal or cancerous tissue and photoactivate melanin or other endogenous pigments located deep within the tissue. As a result, tumors located deep within the body or large, deep tumors can be reached and destroyed. Destruction of these tumors can be done without activating melanin or other endogenous pigments along the path of the light or surrounding the tumor.

In addition to photodynamic destruction of pigmented tissues, such as those in pigmented tumors, the above-described unique features of simultaneous two-photon excitation may be used to achieve improved safety and specificity in the photobleaching of pigmented tissues, such as in moles, freckles, hair follicles and tattoos. The pigments present in such tissues can be activated by simultaneous two-photon activation, as explained supra, and upon activation may become photobleached. Thus, the present invention also uses simultaneous two-photon excitation to specifically target endogenous pigments in such pigmented tissues, thereby causing photobleaching and a desired reduction or elimination of apparent pigmentation.

It is a specific preferred embodiment of the present invention to employ the output of a NIR source, such as the mode-locked titanium:sapphire laser, to induce simultaneous two-photon photoactivation so as to photoactivate melanin, melanin precursors, or other endogenous pigments using light at a wavelength approximately twice that necessary for such conversion using conventional single-photon photoactivation. As explained supra, such NIR light exhibits improved penetration into tissue relative to that used for conventional single-photon photoactivation, and is less likely to produce collateral damage in tissues adjacent to the desired treatment target.

For the sake of simplicity and clarity, the following descriptions of preferred embodiments will focus on photodynamic destruction of pigmented tumor tissues, such as those in melanomas. However, it is important to note that the methods and apparatus described are equally applicable to the photobleaching of pigmented tissues, such as moles or tattoos, differing substantially only in the intended treatment target. In both classes of treatment, it is the photoactivation of the pigment that is fundamentally responsible for the desired therapeutic outcome.

Figure 5:
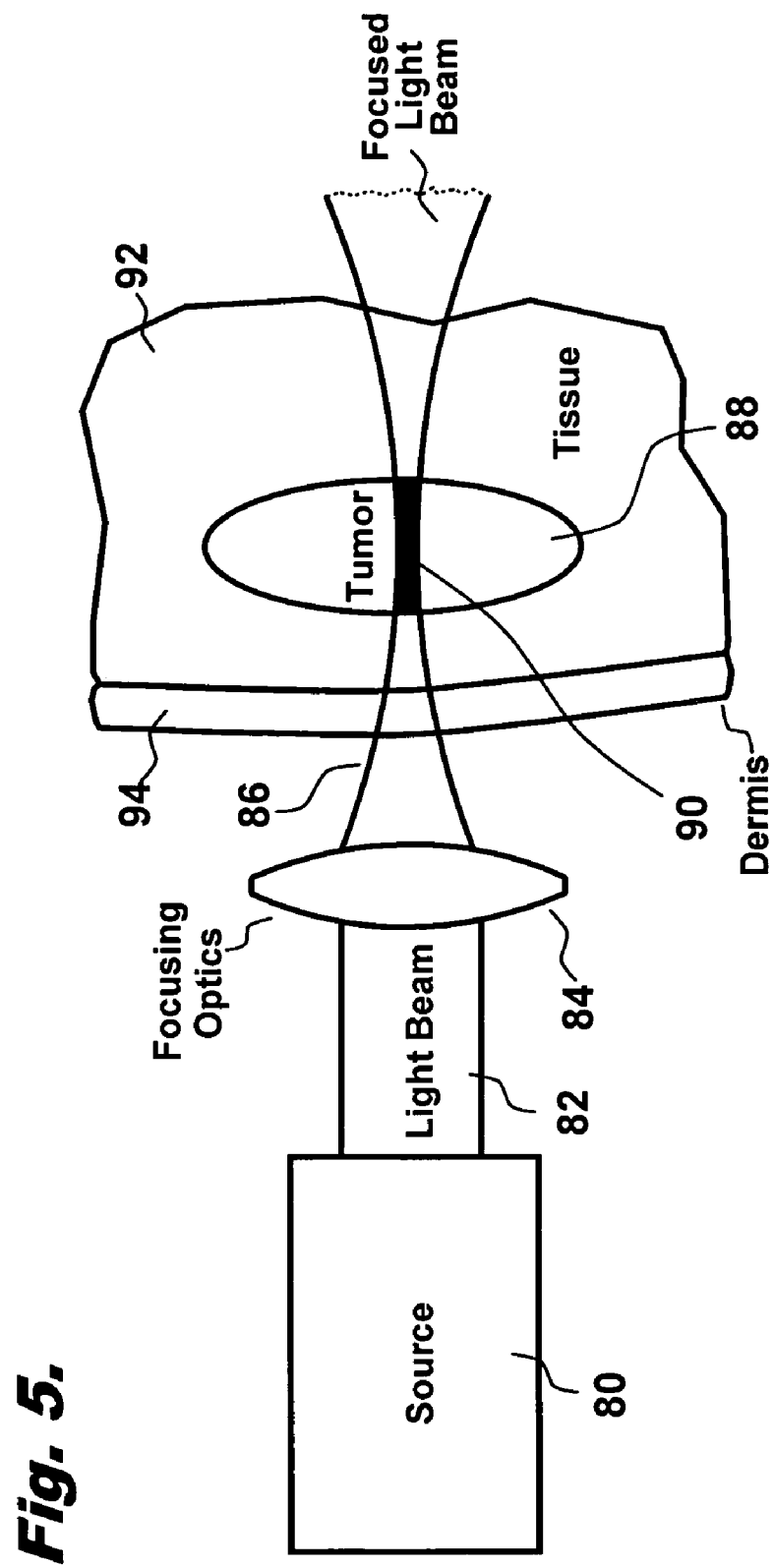
FIG. 5 illustrates an embodiment of the present invention for selective two-photon photoactivation of melanin, melanin-precursors or endogenous pigments using focused light.

Accordingly, a preferred embodiment is shown in FIG. 5. The source 80 produces a beam of light 82 consisting of a rapid series of high peak power pulses of NIR light. For example, standard commercially available mode-locked titanium-sapphire lasers are capable of outputting mode-locked pulses with durations <200 fs and pulse energies of about 1–20 nJ at pulse repetition frequencies in excess of 75 MHz. This source produces a quasi-continuous beam of light having a relatively low average power (up to several Watts) but high peak power (on the order of 100 kW) that is continuously tunable over a NIR wavelength band from approximately 690–1080 nm. The pulse train from the source 80 constitutes a beam of light 82 that is easily focussed using standard optical means, such as reflective or refractive optics 84. The focused beam 86 can then be directed into a tumor 88 or other localized treatment target.

Simultaneous two-photon photoactivation of the melanin, melanin precursors, or other endogenous pigments will be substantially limited to the focal zone 90 of the focused light beam 86 due to the high instantaneous irradiance level that is only present at the focus. Furthermore, regardless of whether melanin, melanin precursors, or another endogenous pigment is present in surrounding healthy tissue 92 or skin 94, insignificant collateral photoactivation, photodamage or conversion into a phototoxic product will occur outside the focal zone 90. This is a consequence of the non-linear relationship between instantaneous optical power and simultaneous two-photon excitation, which limits significant excitation to the focal zone 90. Even if melanin, melanin precursors, or another endogenous pigment is present outside of the focal zone 90, excitation intensities are below that necessary to produce significant photoactivation.

The apparatus of the present invention can also include, for example, a focusing apparatus for focusing the light throughout a range of focal lengths extending from a surface of the tissue to a depth substantially beyond the surface. The source of light and focusing apparatus cooperate to promote simultaneous two-photon excitation of the pigment at controllable locations throughout the volume of tissue.

By scanning the location of the focus of the beam 86 throughout the volume of the tumor 88, complete photoactivation of the melanin, melanin precursors, or other endogenous pigments into a phototoxic product throughout the tumor 88 can be effected. This scanning action can be produced by changing the position of the focus 86 relative to the tumor 88, or by moving the tumor 88 relative to a stationary focus 86 location. The quality of the focal region 90 of the focused light beam 86 may be improved by pre-expanding the light beam 82, using a beam expander or other device, prior to focusing using standard optical means.

This scanning can be done, for example, by positioning a focus of a beam of light over a range of positions so that a focal plane of the light beam occurs at a site located between a surface of the tissue and a point substantially beyond the tissue surface. As a result, treating the particular volume of tissue may extend to penetrate deep within the tissue. This scanning can further include varying, while the beam of light is extant, the radial position of the focal plane within the tissue, thereby to photoactivate the endogenous pigment at a multiplicity of positions between the tissue surface and a position located substantially beyond the tissue surface.

Figure 6:
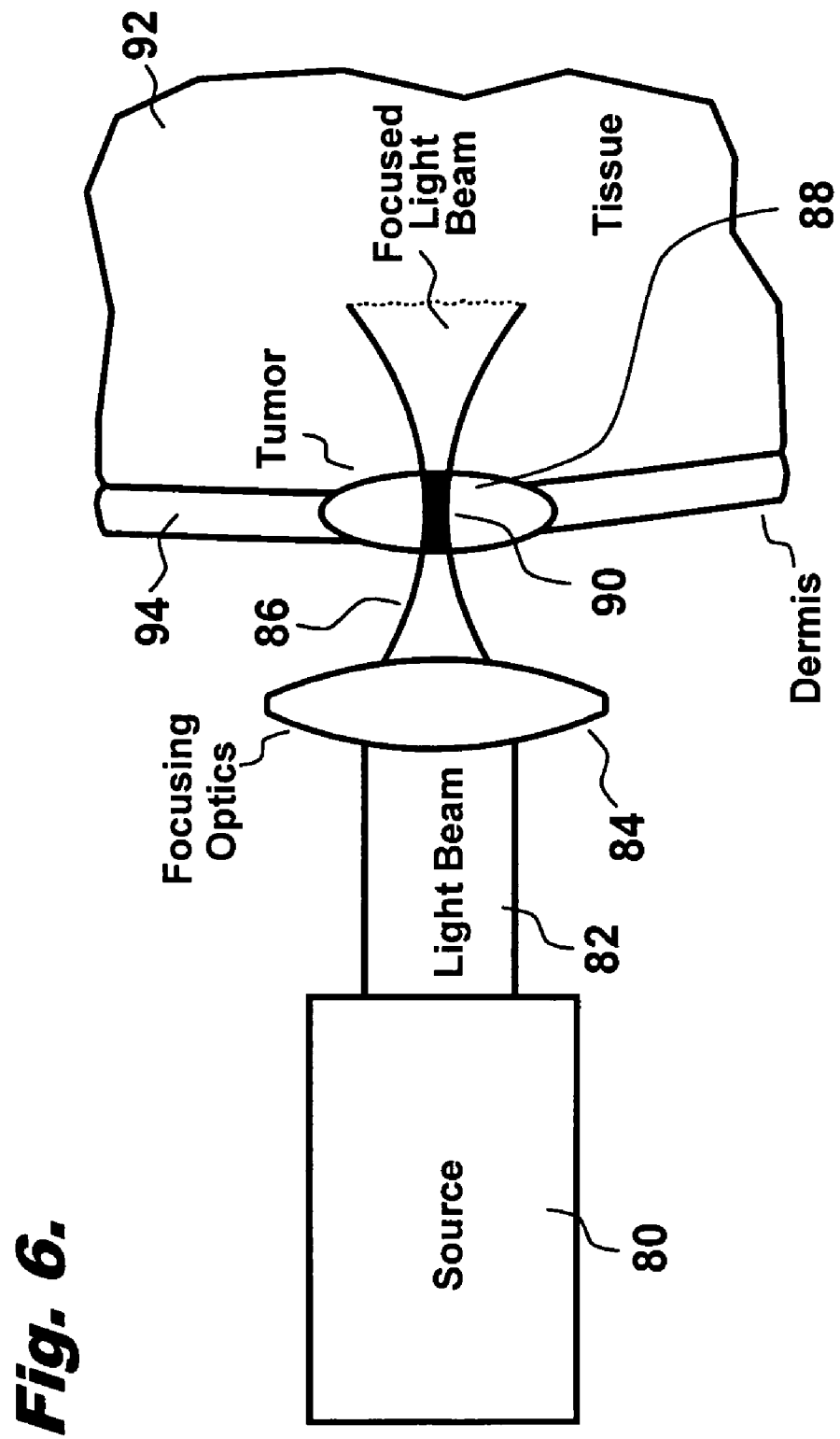
FIG. 6 illustrates an another embodiment for selective two-photon photoactivation of melanin, melanin-precursors, or endogenous pigments using focused light.
Figure 7:
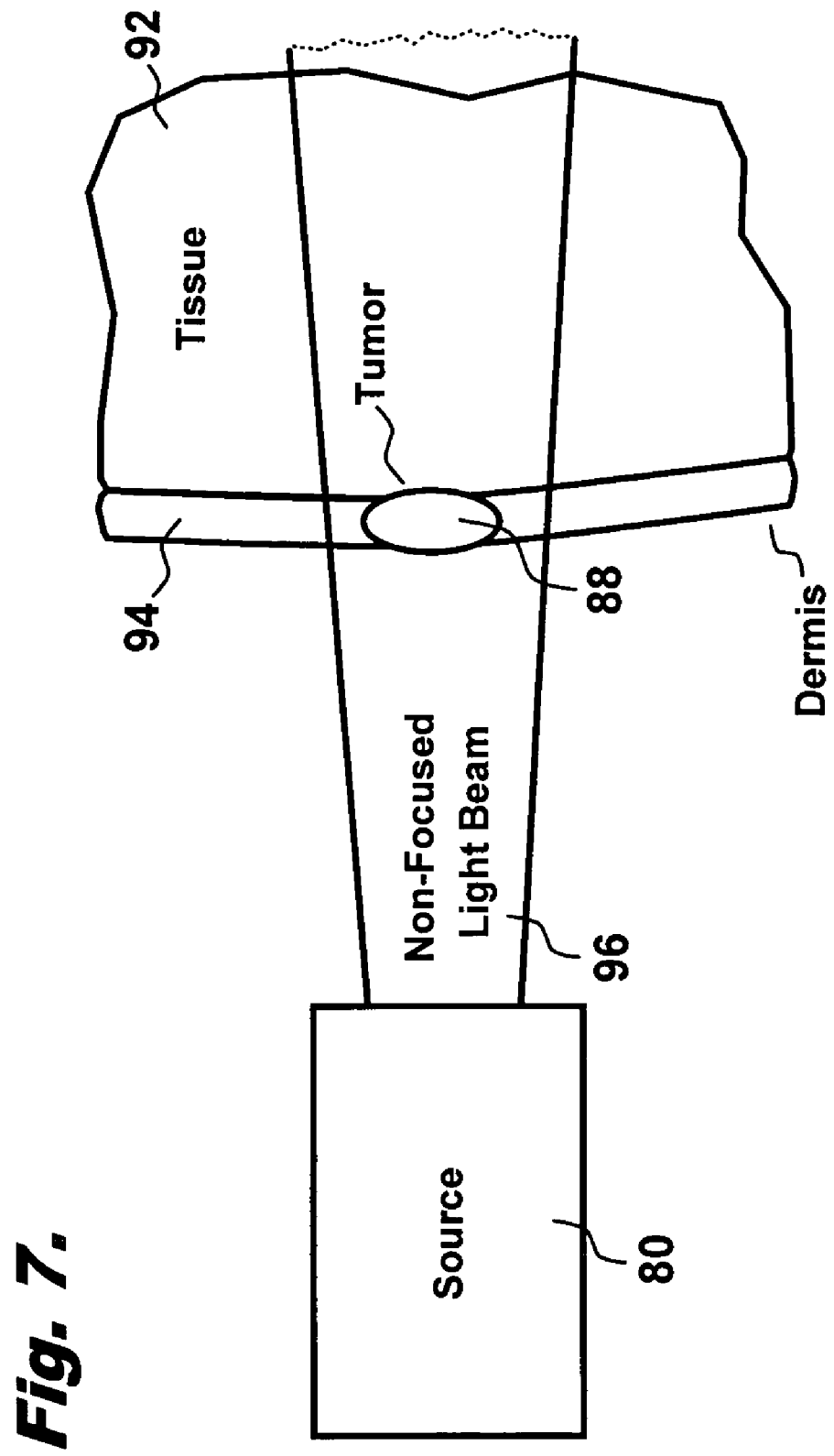
FIG. 7 illustrates a further embodiment for selective two-photon photoactivation of melanin, melanin-precursors, or endogenous pigments using non-focused light.

The simultaneous two-photon photoactivation embodiment of the present invention has several variations for the treatment of topical tissues, as shown in FIG. 6 and in FIG. 7. For example, the non-damaging nature of focused NIR light, shown in FIG. 6, or of non-focused NIR light, shown in FIG. 7, allows photoactivation of melanin or other endogenous pigments at topical locations without risk to underlying or surrounding tissues.

Focused simultaneous two-photon photoactivation of melanin or other endogenous pigments for topical therapy, as shown in FIG. 6, is effected when a beam of light 82 from a source 80 is focused 86 onto a tumor 88 or other localized treatment target using standard optical means, such as reflective or refractive optics 84. In this manner, photoactivation of the melanin, melanin precursors, or other endogenous pigments into a phototoxic product occurs only at the focal zone 90. The surrounding healthy tissue 92 and skin 94 are unaffected in this process, even if they also contain melanin, melanin precursors, or another endogenous pigment, since photoactivation is substantially limited to the focal zone 90. As described previously, a scanning action can be used to effect photoactivation of the melanin, melanin precursor, or other endogenous pigment into a phototoxic product throughout the volume of the tumor 88.

Non-focused simultaneous two-photon photoactivation of melanin, melanin precursors, or other endogenous pigments for topical therapy, as shown in FIG. 7, is effected when a non-focused or expanded beam of light 96 from a source 80 is directed onto a topical tumor 88 or other localized treatment target. This beam of light 96 may have a cross sectional area smaller than, equal to, or larger than that of the tumor 88. Since melanin, melanin precursors, or other endogenous pigments are present in substantially higher levels in the tumor 88, the therapeutic action will be substantially limited to the volume of the tumor 88. Since the beam of light 96 is non-damaging to tissues that do not contain a significant concentration of pigment, damage to surrounding healthy tissue 92 and skin 94 is avoided. This embodiment may be particularly useful when the exact location, size and shape of the tumor 88 are not known, or when it is otherwise undesirable to carefully control the location of application of the beam of light 96, since careful control of the location of the beam of light 96 is not critical for successful administration of this therapeutic regime. When non-focused light is used, employment of extremely high peak power excitation sources, such as Q-switched lasers or regeneratively amplified mode-locked lasers, may be beneficial due to their exceptionally high peak radiant power (which is in the GW range) that will thereby afford a high instantaneous irradiance over a large area.

Figure 8:
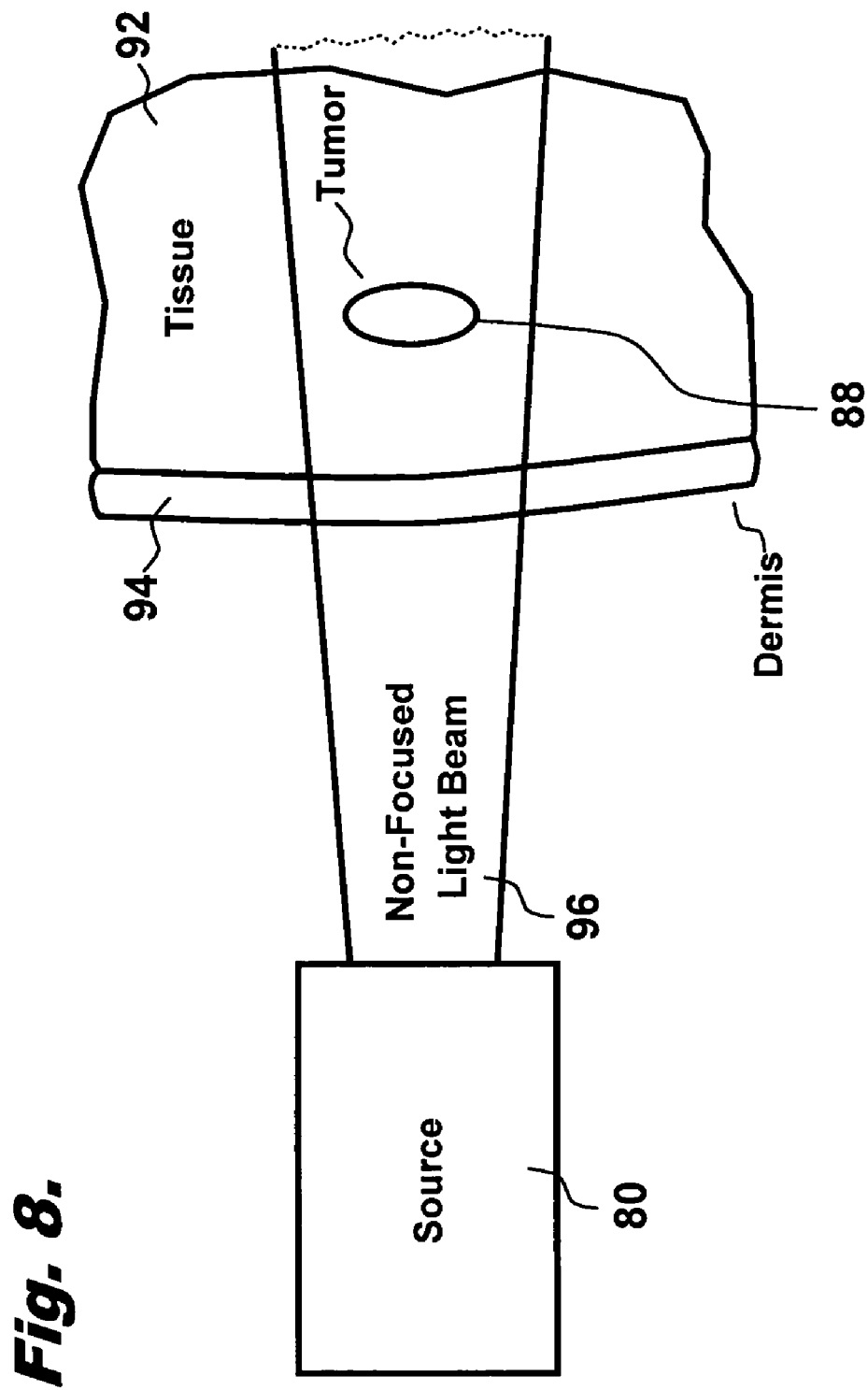
FIG. 8 illustrate still another embodiment for selective two-photon photoactivation of melanin, melanin-precursors, or endogenous pigments in a subsurface tissue using non-focused light.

A final related variation of this preferred embodiment for simultaneous two-photon photoactivation is shown in FIG. 8, where a non-focused or expanded beam of light 96 from a source 80 is directed onto a tumor 88 or other localized treatment target located below the skin's surface. This beam of light 96 may have a cross sectional area smaller than, equal to, or larger than that of the tumor 88. Since melanin, melanin precursors, or other endogenous pigments are present in substantially higher levels in a tumor 88, the therapeutic action will be substantially limited to the volume of the tumor 88. Since the beam of light 96 is non-damaging to tissues that do not contain a significant concentration of pigment, damage to surrounding healthy tissue 92 and skin 94 is avoided. This embodiment may also be particularly useful when the exact location, size and shape of the tumor 88 are not known, or when it is otherwise undesirable to carefully control the location of application of the beam of light 96, since careful control of the location of the beam of light 96 is not critical for successful administration of this therapeutic regime. As in the previous non-focused embodiment, employment of extremely high peak power excitation sources may be beneficial due to their exceptionally high peak radiant power and potential high instantaneous irradiance over a large area.

Preferably, the simultaneous two-photon excitation will be produced by an ultrashort pulsed NIR laser light having a wavelength of from approximately 450 nm to 1400 nm with a pulse width of from approximately 25 fs to 10 ns and a greater than approximately 1 kHz pulse repetition frequency. Such laser light can be produced by a mode-locked titanium:sapphire laser or related laser sources.

The extent and duration of excitation affected with such sources will be controlled by varying the location, irradiance and duration of application of the light.

The effectiveness of the therapeutic outcome may be markedly increased by simultaneous photoactivation and localized heating (hyperthermia) of the treatment site. Such heating occurs as a secondary effect of illumination with laser light, and may also be controlled by varying the location, irradiance and duration of application of the light, so as to yield heating in the treatment zone of 2–10° C. above normal temperatures. For example, application of light at intensities of 150–3000 mW/cm$^2$ may be used to produce such desirable hyperthermia. Alternately, secondary thermal sources, such as infrared lamps or warm fluid baths, may be used to effect such desirable hyperthermia at the treatment site.

While the foregoing disclosure has primarily focused on example therapeutic applications using two-photon excitation of agents with ultrashort pulsed NIR light produced by mode-locked titanium:sapphire lasers, the present invention is not limited to such excitation nor to such narrowly defined optical sources. In fact, aspects of the present invention are applicable when optical excitation is effected using linear or other non-linear methods. For example, various other optical sources are applicable, alone or in combination, such as continuous wave and pulsed lamps, diode light sources, semiconductor lasers; other types of gas, dye, and solid-state continuous, pulsed, or mode-locked lasers, including: argon ion lasers; krypton ion lasers; helium-neon lasers; helium-cadmium lasers; ruby lasers; Nd:YAG, Nd:YLF, Nd:YAP, Nd:YVO4, Nd:Glass, and Nd:CrGsGG lasers; Cr:LiSF lasers; Er:YAG lasers; F-center lasers; Ho:YAG and Ho:YLF lasers; copper vapor lasers; nitrogen lasers; optical parametric oscillators, amplifiers and generators; regeneratively amplified lasers; chirped-pulse amplified lasers; and sunlight.

In an alternative embodiment, an exogenous photodynamic agent can be added to the patient to be activated in conjunction with the endogenous pigments. "Exogenous" agents are photoactive materials not pre-existent in a patient or other target which are for example administered for the purpose of increasing efficiency of conversion of optical energy into a therapeutic process. Examples of such exogenous agents include Rose Bengal, psoralen derivatives, indocyanine, Lutex, Sn(ET$_2$) and various porphyrin derivatives, including porfimer sodium and benzoporphyrin derivative. Preferably, the targeted tissue is pretreated with the exogenous agent so that it retains a therapeutic concentration of the agent when the tissue is treated with light so as to promote simultaneous two-photon activation of the agent. Alternatively, the agent can be added at other times during the process. Upon administration and accumulation in targeted tissue, such agents can be used to efficiently interact with NIR light so as to kill tissue by Type I or Type II PDT mechanisms. Such killing can be used to augment or supplement killing of pigmented tissues using endogenous photoactive agents as described supra.

Another alternate embodiment of the present invention is directed to the thermal destruction of melanomas and other pigmented lesions.

Melanomas are usually dramatically darker than surrounding healthy tissue. The dark color associated with melanomas is caused by increased production of melanin by tumor cells. Melanin is a strong absorber of ultraviolet (UV) and visible light, and normally protects cells from the deleterious effects of solar UV radiation. For example, FIG. 2 shows that melanin is highly absorptive at wavelengths shorter than approximately 1000 nm. In contrast, hemoglobin has minimal absorbance above 450 nm. The high concentration of melanin in most melanoma cells makes them capable of strongly and selectively absorbing light at wavelengths longer than 450 nm and shorter than 1000 nm. Thus, illumination of melanoma cells with light at such wavelengths will produce much more heat in those cells as compared to cells in less pigmented tissue.

Currently, laser illumination is used in cosmetic applications to remove unwanted hair. Laser hair removal is accomplished because there is more pigment in the hair follicles than in surrounding tissue. Therefore, when a laser illuminates the pigmented hair follicle, it absorbs much more of the light, causing localized heating. The localized hyperthermia thereby created in the bulb of the hair follicle kills the hair follicle while sparing surrounding tissue (which is not heated to a significant extent by the laser illumination).

Figure 9:
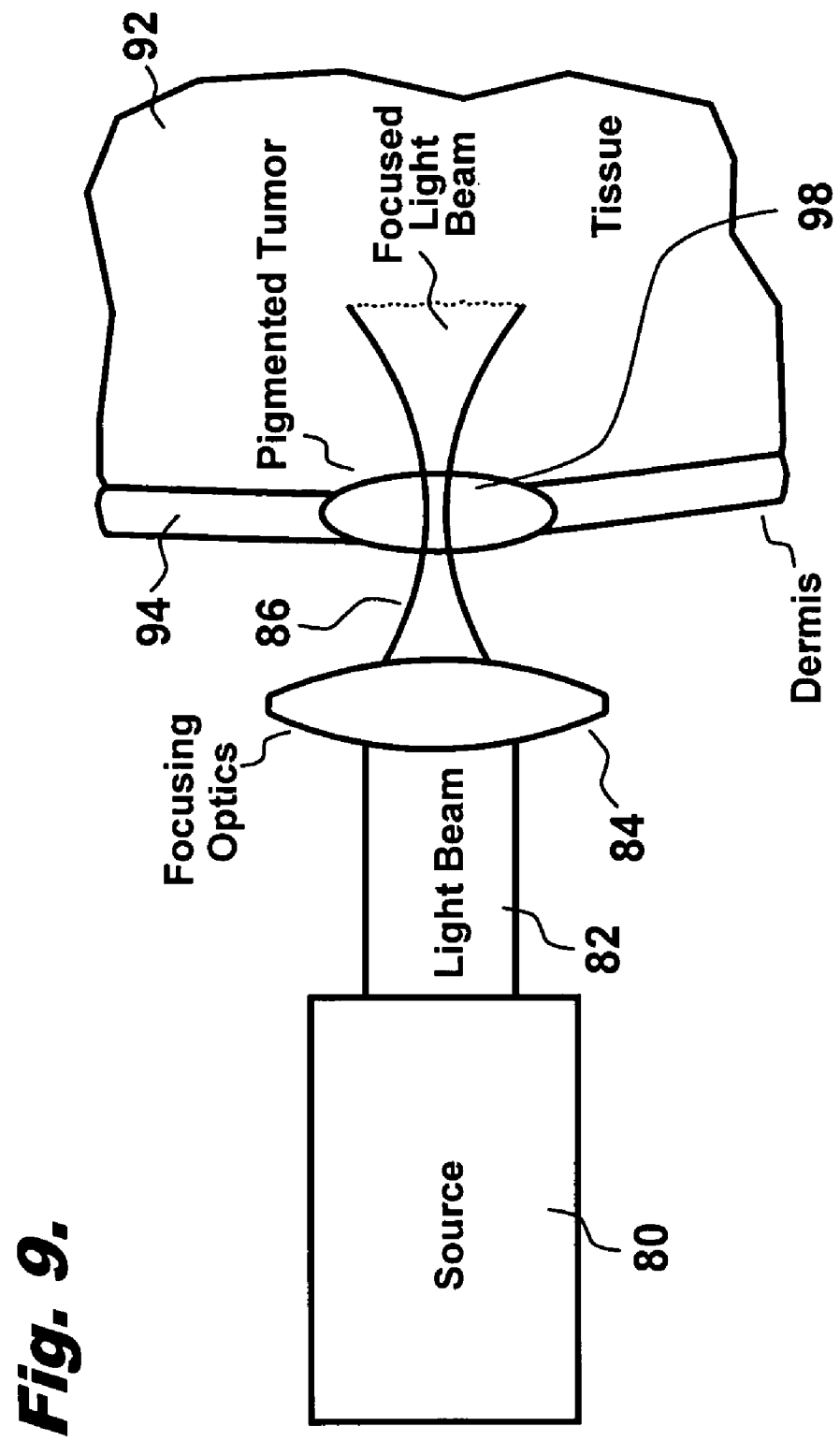
FIG. 9 illustrates an alternate embodiment for the present invention wherein a focused light beam is used to thermally overload and kill pigmented tumor cells.
Figure 10:
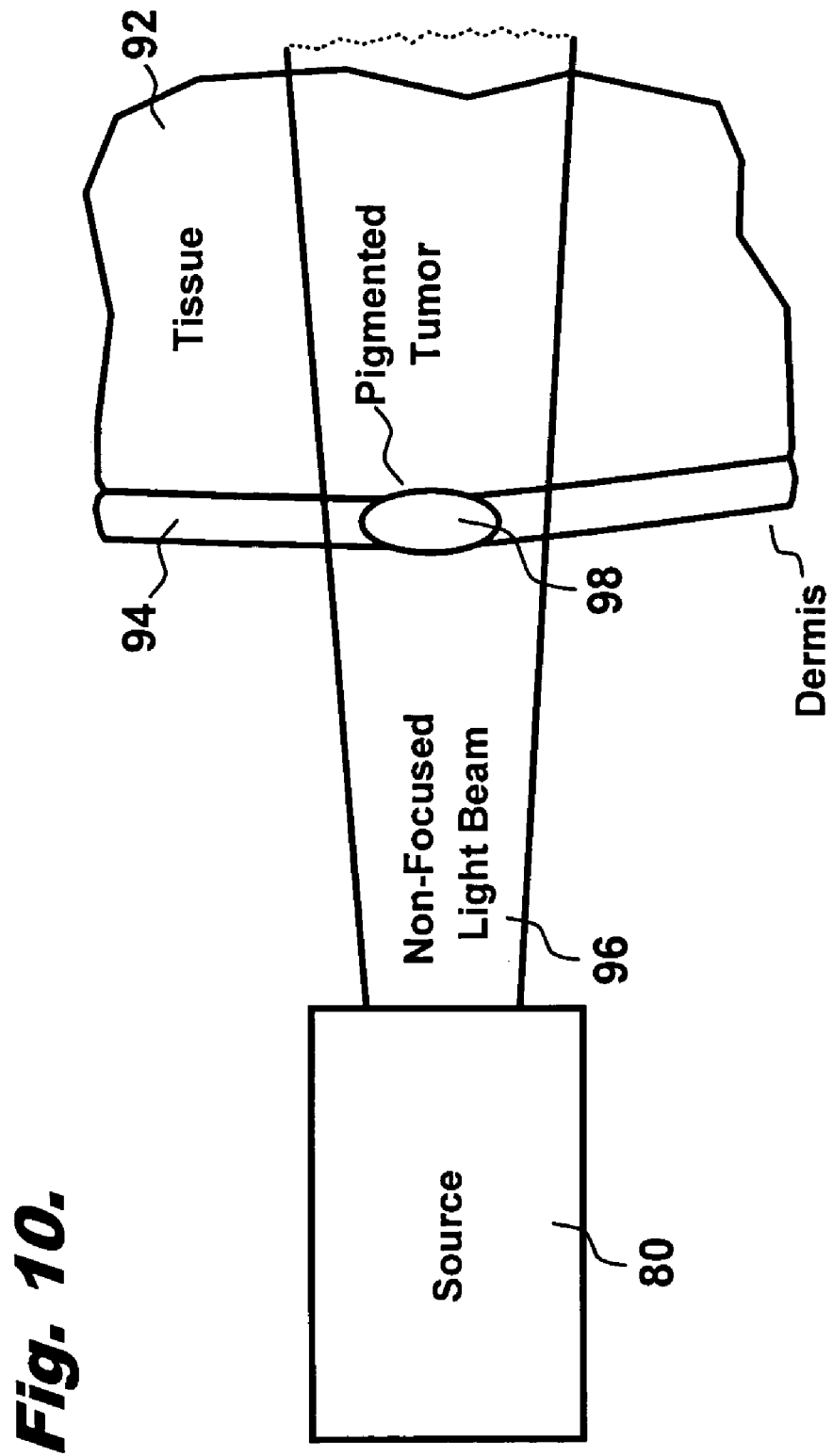
FIG. 10 illustrates another alternate embodiment for the present invention wherein a non-focused light beam is used to thermally overload and kill pigmented tumor cells.

The inventors of the present application have discovered a process to kill pigmented tumor cells by thermally overloading them whereas the relatively unpigmented cells in healthy tissues surrounding the tumor are spared. FIGS. 9 and 10 illustrate such an alternate embodiment for the present invention wherein a focused light beam 86 (FIG. 9) and a non-focused light beam 96 (FIG. 10), respectively, are used to kill pigmented tumor cells 98. Such pigmented tumor cells 98 may be located at the surface of tissue 92 to be treated, or may be located significantly below the surface. Illumination of pigmented tumor cells 98 may be effected using a continuous wave or pulsed laser source operating in either of two wavelength bands between approximately 450 and 800 nm and between approximately 800 and 1400 nm.

For wavelengths between 450 and 800 nm, direct linear excitation of melanin is used to selectively promote thermal overload of pigmented tumor cells 98. Light in this band is preferred when pigmented tumor cells 98 are located at the surface of tissue or at depths of approximately 2 mm or less below the surface since such light is not capable of penetrating tissue to significantly greater depths. For such excitation, it is preferred that illumination be effected via application of one or more short pulses of light having a pulse duration of 10 ns (nanoseconds) or less, and more preferably of 10 ps (picoseconds) or less. Use of such short duration pulses reduces thermal loss to surrounding tissues, thereby improving efficiency in selective thermal overload of the pigmented tumor cells 98. It is further preferred that the wavelength of this light be between approximately 600 and 800 nm to afford improved specificity for excitation of melanin relative to hemoglobin. Moreover, it is further preferred that such light be produced by a light source such as a mode-locked titanium:sapphire laser, which is readily able to deliver such light pulses at such wavelengths. A focused light beam 86 is preferable where the location and extent of the lesion is precisely known, since improved control over the extent of the treatment zone is thereby possible. By scanning this focused light beam 86 throughout the volume of the tumor, it is possible to treat the entirety of the pigmented tumor cells 98. However, where the location and extent of the lesion is not precisely known, or where the lesion is exceptionally large, use of a non-focused light beam 96 is preferred to assure that treatment is effected in all of the pigmented tumor cells 98.

For wavelengths between 800 and 1400 nm, excitation of melanin via linear mechanisms and non-linear two-photon mechanisms is used to selectively promote thermal overload of pigmented tumor cells 98. Light in this band is preferred when pigmented tumor cells 98 are located below the surface of tissue at depths of approximately 2 mm or greater since such light is capable of penetrating tissue to such depths. For such excitation, it is preferred that illumination be effected via application of one or more short pulses of light having a pulse duration of 10 ps or less, and more preferably of 1 ps or less. Use of such short duration pulses increases the efficiency of non-linear excitation mechanisms while simultaneously reducing thermal loss to surrounding tissues, thereby improving efficiency in selective thermal overload of the pigmented tumor cells 98. A focused light beam 86 is preferable where the location and extent of the lesion is precisely known, since improved control over the extent of the treatment zone is thereby possible. Use of such a focused light beam 86 improves efficiency of non-linear excitation mechanisms, allowing relatively low energy light sources 80, such as mode-locked titanium:sapphire lasers, to be successfully used. By scanning this focused light beam 86 throughout the volume of the tumor it is possible to treat the entirety of the pigmented tumor cells 98. However, where the location and extent of the lesion is not precisely known, or where the lesion is exceptionally large, use of a non-focused light beam 96 is preferred to assure that treatment is effected in all of the pigmented tumor cells 98. Under such illumination conditions, amplified or other higher energy light sources 80, such as the regeneratively amplified mode-locked titanium:sapphire laser, are preferred so as to increase illumination intensities to levels sufficient to achieve efficient non-linear excitation.

It will be clear that the methods and apparatus described for this alternate embodiment will be equally applicable to the treatment of other pigmented blemishes, such as for example moles, port wine stains, freckles, scars, and tattoos, and for the reduction or elimination of pigments in hair.

While the present invention has been illustrated and described as embodied in general methods and apparatus for killing pigmented tumors by activation of endogenous pigments using optical radiation, it is not intended to be limited to the details shown, since it will be understood that various omissions, modifications, substitutions and changes in the forms and details of the method illustrated and in its operation can be made by those skilled in the art without departing in any way from the spirit of the present invention.

This description has been offered for illustrative purposes only and is not intended to limit the invention of this application, which is defined in the claims below.

What is claimed as new and desired to be protected by Letters Patent is set forth in the appended claims.

The invention claimed is:

1. A method for the treatment of a particular volume of tissue, said volume of tissue containing an endogenous pigment, the method comprising the steps of:
   treating the particular volume of tissue with light to promote a simultaneous two-photon photoactivation of said pigment in the particular volume of tissue, wherein the pigment becomes photochemically activated in the particular volume of tissue.

2. The method of claim 1 wherein the light to promote said simultaneous two-photon photoactivation is a laser light produced by a laser.

3. The method of claim 2 wherein the laser light comprises a train of one or more ultrashort pulses.

4. The method of claim 2 including operating the laser to produce light at a wavelength between approximately 450 nm to 1400 nm.

5. The method of claim 1 wherein the light to promote said simultaneous two-photon photoactivation is a focused beam of light.

6. The method of claim 5 wherein the focused beam of light is focused laser light.

7. The method of claim 6 wherein said particular volume of tissue is located substantially at the tissue surface.

8. The method of claim 6 wherein said particular volume of tissue is located substantially below the tissue surface.

9. The method of claim 1 wherein said step of treating the particular volume of tissue includes positioning a focus of a beam of light over a range of positions so that a focal plane of the light beam occurs at a site located between a surface of the tissue and a point substantially beyond the tissue surface, whereby said step of treating the particular volume of tissue may extend to penetrate deep within the tissue.

10. The method of claim 9 further including varying, while the beam of light is extant, the radial position of the focal plane within the tissue, thereby to photoactivate the endogenous pigment at a multiplicity of positions between the tissue surface and a position located substantially beyond the tissue surface.

11. The method of claim 1 wherein said endogenous pigment becomes photoactivated in said particular volume at a controllable position substantially beyond a tissue surface.

12. The method of claim 1 further comprising the step of controlling the photoactivation by varying the location, irradiance and duration of said light.

13. The method of claim 1 wherein the light to promote said simultaneous two-photon excitation of the endogenous pigment is a non-focused beam of light.

14. The method of claim 13 wherein said particular volume of tissue is located substantially at the tissue surface.

15. The method of claim 13 wherein said particular volume of tissue is located substantially below the tissue surface.

16. The method of claim 1 wherein said endogenous pigment is selected from the group comprising melanin, melanin precursors, carotenes, porphyrins, and various tattoo dyes.

17. The method of claim 16 wherein said melanin precursors are selected from the group comprising 5-S-cysteinyldopa (5-SCD) and 5,6-dihidroxyindole (DHI), dopa, dopa semiquinone, leucodopachrome, dopachrome, eumalanins, pheomelanins, sepia melanins, and 5,6-dihydroxyindole-2-carboxylic acid.

18. The method of claim 16 wherein said porphyrins include hemoglobin.

19. A method for producing a photoactivated product in a particular volume of a material, the method comprising treating the particular volume of the material with light to promote a simultaneous two-photon excitation of an endogenous pigment contained in the particular volume of the material, wherein the pigment becomes a photoactivated product in the particular volume of the material.

20. The method of claim 19 wherein the light to promote said simultaneous two-photon photoactivation is a laser light produced by a laser.

21. The method of claim 20 wherein the laser light comprises a train of one or more ultrashort pulses.

22. The method of claim 20 including operating the laser to produce light at a wavelength between approximately 450 nm to 1400 nm.

23. The method of claim 19 wherein the light to promote said simultaneous two-photon photoactivation is a focused beam of light.

24. The method of claim 23 wherein the focused beam of light is focused laser light.

25. The method of claim 24 wherein said particular volume of material is tissue located substantially at the surface of said material.

26. The method of claim 24 wherein said particular volume of material is tissue located substantially below the surface of said material.

27. The method of claim 19 wherein said step of treating the particular volume of material includes positioning a focus of a beam of light over a range of positions so that a focal plane of the light beam occurs at a site located between a surface of the material and a point substantially beyond the material surface, whereby said step of treating the particular volume of material may extend to penetrate deep within the material.

28. The method of claim 27 further including varying, while the beam of light is extant, the radial position of the focal plane within the material, thereby to photoactivate the endogenous pigment at a multiplicity of positions between the material surface and a position located substantially beyond the material surface.

29. The method of claim 19 wherein said endogenous pigment becomes photoactivated in said particular volume at a controllable position substantially beyond a material surface.

30. The method of claim 19 further comprising the step of controlling the photoactivation by varying the location, irradiance and duration of said light.

31. The method of claim 19 wherein the light to promote said simultaneous two-photon excitation of the endogenous pigment is a non-focused beam of light.

32. The method of claim 31 wherein said particular volume of material is located substantially at the surface of said material.

33. The method of claim 31 wherein said particular volume of material is tissue located substantially below the surface of said material.

34. The method of claim 19 wherein said endogenous pigment is selected from the group comprising melanin, melanin precursors, carotenes, porphyrins, and various tattoo dyes.

35. The method of claim 34 wherein said melanin precursors are selected from the group comprising 5-S-cysteinyldopa (5-SCD) and 5,6-dihidroxyindole (DHI), dopa, dopa semiquinone, leucodopachrome, dopachrome, eumalanins, pheomelanins, sepia melanins, and 5,6-dihydroxyindole-2-carboxylic acid.

36. The method of claim 34 wherein said porphyrins include hemoglobin.

37. A method for treatment of tissue wherein the tissue includes an endogenous pigment, the method comprising the steps of:
  directing light to specific regions of interest within the tissue, including regions substantially below a tissue surface, said light being selected to penetrate the tissue and to promote two-photon excitation substantially only at a focal zone;
  controlling the location of said focal zone over a range of depths within said tissue; and
  using two-photon excitation, photoactivating said pigment over said range of depths within said tissue, thereby producing a photoactivated product substantially only at the focal zone.

38. The method of claim 37 wherein said directing step includes directing a laser light produced by a laser to said regions of interest.

39. The method of claim 38 wherein the laser light comprises a train of one or more ultrashort pulses.

40. The method of claim 38 including operating the laser to produce light at a wavelength between approximately 450 nm to 1400 nm.

41. The method of claim 37 wherein the light to promote said two-photon photoactivation is a focused beam of light.

42. The method of claim 41 wherein the focused beam of light is focused laser light.

43. The method of claim 42 wherein said regions of interest are located substantially at the tissue surface.

44. The method of claim 42 wherein said regions of interest are located substantially below the tissue surface.

45. The method of claim 42 further comprising the step of scanning said regions of interest with said focused beam of light to promote two-photon excitation throughout said regions of interest.

46. The method of claim 37 wherein said endogenous pigment becomes photoactivated in said focal zone at a controllable position substantially beyond a tissue surface.

47. The method of claim 37 wherein said two-photon photoactivation is simultaneous two-photon activation.

48. The method of claim 37 further comprising the step of controlling the photoactivation by varying the location, irradiance and duration of said light.

49. The method of claim 37 wherein the light to promote said two-photon excitation of the photoactive agent is a non-focused beam of light.

50. The method of claim 49 wherein said regions of interest are located substantially at the tissue surface.

51. The method of claim 49 wherein said regions of interest are located substantially below the tissue surface.

52. The method of claim 37 wherein said endogenous pigment is selected from the group comprising melanin, melanin precursors, carotenes, porphyrins, and various tattoo dyes.

53. The method of claim 52 wherein said melanin precursors are selected from the group comprising 5-S-cysteinyldopa (5-SCD) and 5,6-dihidroxyindole (DHI), dopa, dopa semiquinone, leucodopachrome, dopachrome, eumalanins, pheomelanins, sepia melanins, and 5,6-dihydroxyindole-2-carboxylic acid.

54. The method of claim 52 wherein said porphyrins include hemoglobin.

55. A method for treatment of a particular volume of tissue, said volume of tissue containing an endogenous pigment and an exogenous photodynamic agent, the method comprising the steps of:
  treating the particular volume of tissue with light to promote a simultaneous two-photon photoactivation of said pigment and said agent in said particular volume of tissue, wherein the pigment becomes photochemically converted into a phototoxic product in the particular volume of tissue and said photodynamic agent becomes photoactivated in the particular volume of tissue.

56. The method of claim 55 wherein said exogenous photodynamic agent is selected from the group comprising Rose Bengal, psoralen derivatives, indocyanine, Lutex, $Sn(ET)_2$, and various porphyrin derivatives, including porfimer sodium and benzoporphyrin derivative.

57. The method of claim 55 wherein the particular volume of tissue is pretreated with said exogenous photodynamic agent such that the particular volume of tissue retains a portion of said agent at the time the particular volume of tissue is treated with light so as to promote simultaneous two-photon activation of said agent.

58. The method of claim 1 further comprising the step of heating said volume of tissue using said light so to produce a hyperthermic effect and controlling the hyperthermic effect by varying the location, irradiance and duration of said light so as to augment the effectiveness of said photoactivation.

59. The method of claim 19 further comprising the step of heating said volume of material using said light so to produce a hyperthermic effect and controlling the hyperthermic effect by varying the location, irradiance and duration of said light so as to augment the effectiveness of said photoactivation.

60. The method of claim 1 wherein said photochemical activation of said pigment includes conversion of said pigment into a phototoxic product.

61. The method of claim 1 wherein said photochemical activation of said pigment includes photobleaching of the pigment in said tissue.

62. The method of claim 61 wherein said tissue is selected from the group comprising moles, freckles, hair follicles and tattoos.

63. The method of claim 19 wherein said photoactivated product is a phototoxic product.

64. The method of claim 19 wherein said photoactivation of said pigment includes photobleaching of the pigment in said material.

65. The method of claim 64 wherein said material is selected from the group comprising moles, freckles, hair follicles and tattoos.

66. The method of claim 37 wherein said photoactive product is a phototoxic product.

67. The method of claim 37 wherein said photoactivating of said pigment includes photobleaching of said pigment in said tissue.

68. The method of claim 67 wherein said tissue is selected from the group comprising moles, freckles, hair follicles and tattoos.

* * * * *